United States Patent [19]

Sumino et al.

[11] Patent Number: 4,578,336

[45] Date of Patent: Mar. 25, 1986

[54] PRODUCING NUCLEOSIDES

[75] Inventors: Yasuhiro Sumino, Kobe; Koji Sonoi, Suita; Muneharu Doi, Takarazuka, all of Japan

[73] Assignee: Takeda Chemical Industries, Ltd., Osaka, Japan

[21] Appl. No.: 444,457

[22] Filed: Nov. 24, 1982

[30] Foreign Application Priority Data

Nov. 27, 1981 [JP] Japan ............................ 56-191033

[51] Int. Cl.$^4$ ............................................ C12P 19/40
[52] U.S. Cl. ...................................... 435/88; 435/253; 435/313; 435/813; 435/818; 435/832; 435/839
[58] Field of Search ................... 435/85, 87, 253, 313, 435/88, 813, 818, 832, 839

[56] References Cited

U.S. PATENT DOCUMENTS

| | | | |
|---|---|---|---|
| 2,038,451 | 4/1936 | Schattaneck | 435/818 |
| 3,111,459 | 11/1963 | Motozaki et al. | 435/88 |
| 3,535,207 | 10/1970 | Shiro et al. | 435/85 |
| 3,616,207 | 10/1971 | Suita et al. | 435/88 |
| 3,625,825 | 12/1971 | Shibai et al. | 435/88 |
| 3,846,246 | 1/1974 | Midorikawa et al. | 435/818 |
| 3,912,587 | 10/1975 | Enei et al. | 435/832 |
| 3,960,660 | 6/1976 | Enei et al. | 435/88 |

FOREIGN PATENT DOCUMENTS 0662009  4/1963  Canada .................................... 435/88

OTHER PUBLICATIONS

Isamu Shiio and Kenji Ishii, Journal of Biochemistry (Japan), vol. 69, pp. 339–347 (1971).
Hiroshi Matsui et al.; Agricultural and Biological Chemistry, 43, 393~394 (1979).
Masataka Tate, Hiroshiro Shibai and Kaetsu Kobayashi; Ann. Meet. Agricultural an Chemical Society of Japan (1976) Abstract P.355.

*Primary Examiner*—Thomas G. Wiseman
*Assistant Examiner*—M. Moskowitz
*Attorney, Agent, or Firm*—Wenderoth, Lind & Ponack

[57] ABSTRACT

In a fermentation procedure for the production of nucleosides i.e. inosine and/or guanosine using an adenine-requiring microorganism, the fermentation is carried out by allowing a source of adenine to be present in the medium in an excess amount over the amount of adenine that would be conductive to a maximum yield of inosine and/or guanosine in aerobic culture using ordinary air, and cultivating the microorganism while an oxygen-rich gas is bubbled into the medium. Thus, inosine and/or guanosine are accumulated in high yield in the fermentation broth.

1 Claim, No Drawings

PRODUCING NUCLEOSIDES

This invention relates to an improvement in producing nucleosides i.e. inosine, guanosine or both of them.

Inosine and guanosine are important as starting compounds for the synthesis of drugs, flavorant 5'-ribonucleotides, etc. and it is industrially a worthwhile object to produce these compounds at low cost on a large production scale.

In a conventional fermentation procedure for the production of inosine and/or guanosine using an adenine-requiring microorganism, it was necessary to control the amount of the adenine source to be added to the culture medium within a certain range, and it is known that if the adenine source is added in an excess amount over such range, the yield of inosine and/or guanosine will be adversely affected [Refer, for example, to Journal of Biochemistry (Japan) 69, p. 342 (1971) and Agricultural and Biological Chemistry 43, p. 393 (1979)].

However, the present inventors conducted intensive research to develop a new type of inosine and/or guanosine fermentation which would not be subject to the above limitations, and found that if an inosine and/or guanosine-producing microorganism is cultivated in a medium containing an excess of an adenine source with an oxygen-rich gas being fed to the medium, the yield of inosine and/or guanosine will be remarkably increased. This finding plus subsequent studies have resulted in the present invention.

This invention is, therefore, concerned with a method of producing inosine and/or guanosine comprising cultivating an adenine-requiring and inosine and/or guanosine-producing microorganism in a culture medium to cause the microorganism to elaborate and accumulate inosine and/or guanosine in a fermentation broth, and recovering the inosine and/or guanosine from the broth, wherein the improvement comprises allowing a source of adenine to be present in the medium in an excess amount over the amount of adenine that would be conducive to a maximum yield of inosine and/or guanosine in aerobic culture using ordinary air, and cultivating the microorganism while an oxygen-rich gas is bubbled into the medium.

The adenine source employed in accordance with this invention may be adenine as such or an adenine derivative or a material containing adenine.

Examples of the adenine derivative include adenosine, 5'-adenosine monophosphate, 3'-adenosine monophosphate, 5'-adenosine diphosphate, 5'-adenosine triphosphate, ribonucleic acid, deoxyribonucleic acid, adenylosuccinic acid, etc.

Examples of the material containing adenine include microbial cells (e.g. yeast) and extracts thereof, and other natural organic matters such as beef extract, fish flesh extract, etc.

The amount of adenine that would be conducive to a maximal yield of inosine and/or guanosine in aerobic culture using ordinary air means the amount of an adenine source that will provide a maximal accumulation yield of inosine and/or guanosine under the conventional aerobic cultural conditions. In this connection, it has been mentioned in Journal of Biochemistry (Japan) 69, p. 342 (1971) that the amount of adenine that will provide a maximum accumulation yield of inosine is 50 to 150 μg/ml depending on the strain of microorganism employed, and in Agricultural and Biological Chemistry 43, p. 393 (1979) it is mentioned that the optimum concentration of the adenine source (ribonucleic acid) for the accumulation of guanosine is about 1.4 g/l and, if the concentration of ribonucleic acid exceeds 1.8 g/l the yield of guanosine is drastically reduced. This invention may be practiced using, as the amount of adenine conducive to a maximal yield of inosine and/or guanosine as defined herein, the limit taught by the prior art as set forth in the above-mentioned literature (when the adenine source is other than adenine, the equivalent amount of adenine).

The preferred concentration of the adenine source which is to be incorporated in the medium in the practice of this invention is about 200 to 800 μg/ml as adenine, and preferably about 300 to 500 μg/ml on the same basis.

The time at which the adenine source is added to the medium according to this invention is optional. For example, the entire amount may be previously added to the medium before fermentation is commenced or the adenine source be added in installments as fermentation proceeds.

This invention is carried into practice while a gas containing a larger amount of oxygen than that in ordinary air is bubbled into the medium by a per se conventional method, e.g. aerobic submerged cultural technique.

The oxygen-rich gas employed in the practice of this invention may of course be pure oxygen gas, or may be a gaseous mixture of oxygen and air, or an oxygen-rich gas generated from a molecular sieve process or a membrane separation oxygen generator, for instance.

To supply such a gas containing a higher concentration of oxygen than that in ordinary air, the gas may be constantly fed at a constant calculated rate throughout the fermentation process or automatically fed as the necessary additional amount is monitored from dissolved oxygen data. To supply the oxygen-rich gas, it is possible to feed ordinary air and oxygen from independent nozzles.

When such a gas is supplied at a constant rate throughout the fermentation process in the practice of this invention, the amounts of air and oxygen bubbled into the medium can be determined by the following equations, provided that the feed amount of ordinary air in the conventional process is $Q_o$ (VVM).

$$Q_{AIR} = \frac{100 - C}{79} \times Q_o$$

$$Q_{OXYGEN} = \frac{C - 21}{79} \times Q_o$$

where $Q_{AIR}$ and $Q_{OXYGEN}$ are the amounts (VVM) of air and oxygen, respectively, that are supplied to the medium, and C is the oxygen concentration (%) of a gaseous mixture of oxygen and air. The value C can be arbitrarily determined to be not less than the value $C_o$ calculated from the following experimental equation.

$$C_o = Ad \times 10^3$$

wherein $C_o$ represents the minimum oxygen concentration (%) of a gaseous mixture of oxygen and air, which is needed to obtain the maximum accumulation yield of inosine and/or guanosine when the adenine equivalent concentration of adenine source in the medium is Ad (weight/volume, %). In general, $Q_o$ is about 0.2 to 5 VVM.

The microorganism employed in accordance with this invention may be any adenine-requiring microorganism that is able to elaborate inosine and/or guanosine. Examples of such microorganism include microorganisms belonging to the genus Bacillus, the genus Brevibacterium and the genus Corynebacterium. In terms of species, there may be mentioned *Bacillus pumilus, Bacillus subtilis,* etc. as examples of microorganisms of the genus Bacillus. More particularly, *Bacillus pumilis* No. 148-S-16 (FERM BP-6, IFO 12483), *Bacillus pumilus* No. 158-A-17 (FERM BP-7, IFO 12477), *Bacillus subtilis* ATCC 19221 (IFO 14123), *Bacillus subtilis* ATCC 13956 (IFO 14124), etc. may be mentioned. As species of the genus Brevibacterium, there may be mentioned *Brevibacterium ammoniagenes,* for instance. More particularly, *Brevibacterium ammoniagenes* ATCC 21477, ATCC 21478, ATCC 21479 and ATCC 21480 may for example be mentioned. As species of the genus Corynebacterium, there may be mentioned *Corynebacterium glutamicum,* which is illustrated by *Corynebacterium glutamicum* ATCC 21266 and ATCC 21296.

The above-mentioned *Bacillus pumilus* No. 148-S-16 and *Bacillus pumilus* No. 158-A-17 have been deposited at Institute for Fermentation (IFO), 17–85, Jusohonmachi 2-chome, Yodogawa-ku, Osaka, Japan since Jan. 11, 1967 under the accession numbers IFO 12483 and IFO 12477, respectively, and deposited since June 4, 1981 at Fermentation Research Institute, Agency of Industrial Science and Technology, Ministry of International Trade and Industry (FRI), 1–3, Yatabecho Higashi 1-chome, Tsukaba-gun, Ibaraki, Japan in accordance with the Budapest Treaty under the accession numbers FERM BP-6 and FERM BP-7, respectively.

The above-mentioned *Bacillus subtilis* ATCC 19221 and *Bacillus subtilis* ATCC 13956 are listed in The American Type Culture Collection (12301 Parklawn Drive, Rockville, Md. 20852) Catalogue of Strains I, Fourteenth Edition, 1980. The *Bacillus subtilis* ATCC 19221 and *Bacillus subtilis* ATCC 13956 have been deposited in Institute for Fermentation, Osaka under the accession numbers IFO 14213 and IFO 14124, respectively.

The above-mentioned *Brevibacterium ammoniagenes* ATCC 21477, ATCC 21478, ATCC 21479 and ATCC 21480, *Corynebacterium glutamicum* ATCC 21266 and ATCC 21296 are listed on the American Type Culture Collection Catalogue of Strains I, Fourteenth Edition, 1980.

As the medium for cultivating such a microorganism in the practice of this invention, any of the media used generally for inosine and/or guanosine fermentation can be employed. For example, the medium may contain as carbon sources various carbohydrates such as starch, glucose, sucrose, etc., monohydric or polyhydric alcohols such as glycerin, methanol, ethanol, sorbitol, etc., fatty acids such as acetic acid, propionic acid, stearic acid, oleic acid, etc., oils and fats such as soybean oil, olive oil, fish oil, sperm oil, cottonseed oil, palm oil, lard, etc., n-paraffins such as nonane, decane, undecane, hexadecane, eicosane, pentacosane, etc., and hydrocarbons such as kerosene, gas oil, heavy gas oil, etc. These carbon sources may be used singly or as a mixture. Preferred carbon sources are carbohydrates such as starch, glucose and/or sucrose.

The nitrogen sources incorporated in the medium may for example be organic nitrogen sources such as peptone, soybean flour, corn steep liquor, yeast, meat extract, urea, etc. and inorganic nitrogen sources such as ammonium salts of sulfuric acid, nitric acid, hydrochloric acid, carbonic acid, etc., ammonia gas, aqueous ammonia, etc. These nitrogen sources can be used either singly or as a mixture. In addition, there may also be added to the medium a suitable assortment of inorganic salts necessary for growth of the microorganism, e.g. the sulfates, hydrochlorides, carbonates, nitrates, phosphates, acetates, etc. of calcium, potassium, sodium, magnesium, manganese, iron, copper, zinc, etc., as well as amino acids, vitamins, etc. which are necessary for growth of the microorganism. These nutrients may also be used singly or in combination. If necessary, there may also be added to the medium an antifoam or surfactant such as silicone oil, polyalkylene glycol ether, etc.

Generally, the pH of the medium is preferably selected from the range of pH about 5 to pH about 8. The especially preferred pH range is pH about 5.5 to about 7.5. When the pH of the medium changes beyond the appropriate range during fermentation, it is possible to bring the pH of the medium back into such range by adding an aqueous solution or suspension of alkali hydroxide, calcium carbonate or the like, or ammonia gas, for instance, to the medium.

The incubation temperature should be a temperature suited to growth of the microorganism employed. Generally, it is advantageous to conduct fermentation at about 20° to 60° C. and preferably at about 25° to 45° C.

Regarding the duration of cultivation, the microorganism is cultivated until the yield of inosine and/or guanosine is maximal. Generally, the desired object can be accomplished by cultivating the microorganism for 24 to 144 hours.

Inosine and/or guanosine as elaborated in the fermentation broth according to this invention can be easily recovered from the broth, either independently or as a mixture, by the known purification procedures such as chromatography using an ion exchange resin or activated carbon, precipitation, solvent extraction, etc.

In accordance with this invention, inosine and/or guanosine are accumulated in high yield in the fermentation broth. Therefore, in accordance with the method of this invention, an increased yield of desired inosine and/or guanosine can be attained using presently installed equipment. Moreover, since the broth contains inosine and/or guanosine in high concentrations, the recovery of the desired products is facilitated. In view of the above and other facts, the method of this invention is a commercially advantageous method.

The following examples are further illustrative but by no means limitative of this invention. It should be understood that unless otherwise specified, all percents (%) are weight/volume percents.

EXAMPLE 1

A culture of *Bacillus pumilus* No. 148-S-16 (FERM BP-6, IFO 12483) as grown on a nutrient agar medium containing 100 mg/l of adenine was used to inoculate five 200-ml conical flasks each containing 20 ml of a sterilized seed culture medium composed of 4% glucose, 0.2% urea, 0.1% potassium chloride, 0.006% manganese sulfate (ca. $4H_2O$), 0.2% calcium chloride ($2H_2O$), 0.03% histidine, 200 μg/l biotin, 2% corn steep liquor, 0.25% ribonucleic acid (75% purity) and water. The inoculated flasks were incubated under shaking at 37° C. for 18 hours. The whole amount of the resulting seed culture was transferred to 5-liter jar fermentors each containing 2 liters of a sterilized fermentation medium composed of 2% glucose, 0.4% ammonium sulfate, 0.5% sodium L-glutamate, 0.2% magnesium sulfate (7H$_2$O), 0.1% potassium chloride, 0.2% calcium chloride (2H$_2$O), 0.003% manganese sulfate (ca. 4H$_2$O), 0.03% histidine, 200 μg/l biotin, 0.005% inosine, 2.5% corn steep liquor, a varying amount of ribonucleic acid (75% purity) and water (See Table 1). Each jar fermentor was incubated at 38° C. and 1000 r.p.m. This fermentation was carried out in duplicate, i.e. under the supply of air (0.6 VVM) and under the concurrent supply of air (0.4 VVM) and pure oxygen (0.2 VVM). After the 12th hour of incubation, a separately sterilized 80% glucose solution was continuously fed into the fermentor so that the glucose level in the broth would be maintained at ≦0.2%. The fermentation was continued for 92 hours. The pH of the fermentation medium was maintained at 6.7 by automatic feeding of 25% aqueous ammonia. The resulting fermentation broth was assayed for inosine and guanosine by high performance liquid chromatography. The results are shown in Table 1.

2% glucose, 0.8% ammonium sulfate, 1% sodium L-glutamate, 0.3% magnesium sulfate (7H$_2$O), 0.15% potassium chloride, 0.3% calcium chloride (2H$_2$O), 0.0045% manganese sulfate (ca. 4H$_2$O), 0.045% histidine, 300 μg/l biotin, 0.075% inosine, 7% corn steep liquor, 0.7% ribonucleic acid (75% purity), 1% urea and water. The fermentation was conducted under a concurrent supply of air (0.3 VVM) and pure oxygen (0.3 VVM) in otherwise the same manner as Example 1 for 96 hours. During this period, 1.2 liters of a 80% glucose solution was consumed and a final broth volume of 3 liters was obtained. This broth was assayed for inosine and guanosine by high performance liquid chromatography. The results were 25.3 g/l and 21.6 g/l, respectively.

The cells were filtered off from the above broth and the filtrate was treated with a decolorizing resin and an anion exchange resin in the conventional manner to obtain an inosine and quanoisine fraction. This fraction

TABLE 1

| Concentration of ribonucleic acid (%) | Type of gas fed | Volume of glucose solution fed (l) | Volume of broth at end of fermentation (l) | Output of nucleosides inosine (g/l) | guanosine (g/l) |
|---|---|---|---|---|---|
| 0.25 | Air | 0.382 | 2.10 | 15.1 | 15.5 |
| 0.25 | Air + oxygen | 0.370 | 2.10 | 15.5 | 15.7 |
| 0.45 | Air | 0.456 | 2.25 | 2.2 | 2.4 |
| 0.45 | Air + oxygne | 0.512 | 2.25 | 20.7 | 22.0 |
| 0.65 | Air | 0.568 | 2.38 | 0.4 | 0.6 |
| 0.65 | Air + oxygen | 0.950 | 2.70 | 17.7 | 18.5 |

EXAMPLE 2

Fermentation was conducted in the same manner as Example 1 except that *Bacillus subtilis* ATCC 19221 (IFO 14123) was employed in lieu of *Bacillus pumilus* No. 148-S-16 (FERM BP-6, IFO 12483), provided further that ribonucleic acid (75% purity) was added at the amount as shown in Table 2 and the incubation temperature was 34° C. After the 18th hour, a sterilized 80% glucose solution was added as in Example 1, and the fermentation was continued for 70 hours. The results are shown in Table 2.

was concentrated under reduced pressure to give crude mixed crystals of inosine and guanosine. These mixed crystals were dissolved in water and further purified by adsorption on activated carbon and recrystallization in the per se conventional manner to give 60.6 g of inosine and 52.7 g of guanosine, both as crystals.

EXAMPLE 4

Fermentation in the same manner as Example 1 except that *Bacillus pumilus* No. 158-A-17 (FERM BP-7, IFO 12477) was employed in lieu of *Bacillus pumilus* No. 148-S-16 (FERM BP-6, IFO 12483), provided fur-

TABLE 2

| Concentration ribonucleic acid (%) | Type of gas fed | Volume of glucose solutuon fed (l) | Volume of broth at end of fermentation (l) | Output of inosine and guanosine (g/l) |
|---|---|---|---|---|
| 0.25 | Air | 0.150 | 1.86 | 14.5 |
| 0.25 | Air + oxygen | 0.150 | 1.85 | 14.9 |
| 0.45 | Air | 0.255 | 1.94 | 0.9 |
| 0.45 | Air + oxygen | 0.300 | 2.00 | 23.1 |

EXAMPLE 3

About 100 ml of a seed culture of *Bacillus pumilus* No. 148-S-16 (FERM BP-6, IFO 12483) as obtained using the same procedure and medium as described in Example 1 was used to inoculate a 5-liter jar fermentor containing 2 liters of a sterilized medium composed of ther that adenine was added at the levels of 0.015%, 0.04% and 0.080%. After the 8th hour, a sterilized 80% glucose solution was continuously fed into the fermentor so that the glucose level in the broth would be maintained at ≦1%. The fermentation was continued for 70 hours. Output of inosine was as shown in Table 3.

TABLE 3

| Concentration of adenine (%) | Type of gas fed | Volume of glucose solution fed (l) | Volume of broth at end of fermentation (l) | Output of inosine (g/l) |
|---|---|---|---|---|
| 0.015 | Air (1.0 VVM) | 0.400 | 2.16 | 24.1 |
| 0.015 | Air (0.75 VVM) + oxygen (0.25 VVM) | 0.400 | 2.19 | 22.5 |
| 0.040 | Air (1.0 VVM) | 0.725 | 2.49 | 1.8 |
| 0.040 | Air (0.75 VVM) + | 1.125 | 2.98 | 33.4 |

TABLE 3-continued

| Concentration of adenine (%) | Type of gas fed | Volume of glucose solution fed (l) | Volume of broth at end of fermentation (l) | Output of inosine (g/l) |
| --- | --- | --- | --- | --- |
| 0.080 | oxygen (0.25 VVM) Air (1.0 VVM) | 1.375 | 3.10 | 1.0 |
| 0.080 | Air (0.25 VVM) + oxygen (0.75 VVM) | 1.700 | 3.48 | 28.0 |

What we claim is:

1. A method of producing inosine or guanosine or both inosine and guanosine, comprising cultivating an adenine-requiring microorganism capable of producing inosine or guanosine or both inosine and guanosine, selected from the group consisting of *Bacillus pumilus* No. 148-S-16 (FERM BP-6, IFO 12483), *Bacillus pumilus* No. 158-A-17 (FERM BP-7, IFO 12477), *Bacillus subtilis* ATCC 19221 (IFO 14123) and *Bacillus subtilis* ATCC 13956 (IFO 14124), in a culture medium containing a source of adenine selected from the group consisting of adenine, adenosine, 5'-adenosine monophosphate, 3'-adenosine monophosphate, 5'-adenosine diphosphate, 5'-adenosine triphosphate, ribonucleic acid, deoxyribonucleic acid, adenylosuccinic acid, microbial cells, extracts of microbial cells, beef extract, and fish flesh extract, to cause said microorganism to elaborate and accumulate inosine or guanosine or both inosine and guanosine in a fermentation broth; and recovering the inosine or guanosine or both inosine and guanosine from said broth, wherein the improvement comprises incorporating said source of adenine in said medium in an excess amount over the amount of adenine that would be conducive to a maximum yield of inosine or guanosine or both inosine and guanosine in an aerobic culture if air were used, the amount of said source of adenine in said medium being 200 to 800 μg/ml as adenine, and cultivating said microorganism while air and oxygen are bubbled into said medium in accordance with the following equations:

$$Q_{AIR} = \frac{100 - C}{79} \times Q_o$$

$$Q_{OXYGEN} = \frac{C - 21}{79} \times Q_o$$

wherein $Q_{AIR}$ and $Q_{OXYGEN}$ are the amounts (VVM) of air and oxygen, respectively, that are supplied to said medium, $Q_o$ is 0.2 to 5 VVM, which is the feed amount of air in a conventional process and C is the oxygen concentration (%) of a gaseous mixture of oxygen and air, which is arbitrarily determined to be not less than the value $C_o$ calculated from the following experimental equation:

$$C_o = Ad \times 10^3$$

wherein $C_o$ represents the minimum oxygen concentration (%) of a gaseous mixture of oxygen and air, which is needed to obtain the maximum accumulation yield of inosine or guanosine or both inosine and guanosine when the adenine equivalent concentration of adenine source in the medium is Ad (weight/volume, %).

* * * * *